(12) United States Patent
Backus

(10) Patent No.: US 11,622,852 B2
(45) Date of Patent: Apr. 11, 2023

(54) REPLACEMENT HEART VALVE IMPLANT WITH INFLOW STITCHING

(71) Applicant: BOSTON SCIENTIFIC SCIMED, INC., Maple Grove, MN (US)

(72) Inventor: Andrew J. H. Backus, Santa Cruz, CA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 1017 days.

(21) Appl. No.: 15/597,638

(22) Filed: May 17, 2017

(65) Prior Publication Data
US 2017/0333183 A1 Nov. 23, 2017

Related U.S. Application Data

(60) Provisional application No. 62/337,428, filed on May 17, 2016.

(51) Int. Cl.
*A61F 2/24* (2006.01)

(52) U.S. Cl.
CPC .......... *A61F 2/2409* (2013.01); *A61F 2/2415* (2013.01); *A61F 2/2418* (2013.01); *A61F 2/2436* (2013.01); *A61F 2220/0008* (2013.01); *A61F 2220/0075* (2013.01); *A61F 2250/0069* (2013.01)

(58) Field of Classification Search
CPC ............ A61F 2/2418; A61F 2250/0069; A61F 2220/0075; A61F 2/2409; A61F 2/2436; A61F 2220/0008
See application file for complete search history.

(56) References Cited

U.S. PATENT DOCUMENTS

| 5,411,552 A | 5/1995 | Andersen et al. |
| 2014/0277417 A1* | 9/2014 | Schraut ................. A61F 2/2403 623/2.17 |

(Continued)

FOREIGN PATENT DOCUMENTS

| WO | 2016126524 A1 | 8/2016 |
| WO | 2017027289 A1 | 2/2017 |

OTHER PUBLICATIONS

International Search Report and Written Opinion dated Aug. 16, 2017 for International Application No. PCT/US2017/033160.

*Primary Examiner* — Jerrah Edwards
*Assistant Examiner* — Christine L Nelson
(74) *Attorney, Agent, or Firm* — Seager, Tufte & Wickhem LLP

(57) ABSTRACT

A replacement heart valve implant may include a tubular anchor member actuatable between a delivery and a deployed configuration, the tubular anchor member including an inflow end, an outflow end, and a plurality of anchor member intersection points, and defining a longitudinal axis extending from the inflow end to the outflow end, a plurality of valve leaflets, and a seal member secured to the tubular anchor member at the inflow end. An end surface of each of the plurality of valve leaflets may abut an inner-facing surface of the seal member. The plurality of valve leaflets each define a secured end and a free end. The secured end may be attached to the seal member adjacent the inflow end. The secured end may define the end surface, and the end surface may face toward the outflow end when the plurality of valve leaflets is in an everted position.

5 Claims, 10 Drawing Sheets

(56) References Cited

U.S. PATENT DOCUMENTS

| | | |
|---|---|---|
| 2015/0157455 A1 | 6/2015 | Hoang et al. |
| 2015/0320552 A1 | 11/2015 | Letac et al. |
| 2015/0320556 A1 | 11/2015 | Levi et al. |
| 2016/0199177 A1* | 7/2016 | Spence ................ A61F 2/2409 623/2.38 |

\* cited by examiner

REPLACEMENT HEART VALVE IMPLANT WITH INFLOW STITCHING

CROSS-REFERENCE TO RELATED APPLICATIONS

This application claims priority to U.S. Provisional Application No. 62/337,428, filed May 17, 2016.

TECHNICAL FIELD

The present disclosure pertains to medical devices, and methods for manufacturing and/or using medical devices. More particularly, the present disclosure pertains to configurations of a replacement heart valve.

BACKGROUND

A wide variety of intracorporeal medical devices have been developed for medical use, for example, intravascular use. Some of these devices include guidewires, catheters, medical device delivery systems (e.g., for stents, grafts, replacement valves, etc.), and the like. These devices are manufactured by any one of a variety of different manufacturing methods and may be used according to any one of a variety of methods. Of the known medical devices and methods, each has certain advantages and disadvantages. There is an ongoing need to provide alternative medical devices as well as alternative methods for manufacturing and using medical devices.

SUMMARY

In a first aspect, a replacement heart valve implant may comprise a tubular anchor member actuatable between a delivery configuration and a deployed configuration, the tubular anchor member including an inflow end, an outflow end, and a plurality of anchor member intersection points, and defining a longitudinal axis extending from the inflow end of the tubular anchor member to the outflow end of the tubular anchor member, a plurality of valve leaflets, and a seal member secured to the tubular anchor member at the inflow end of the tubular anchor member. An end surface of each of the plurality of valve leaflets abuts an inner-facing surface of the seal member.

In addition or alternatively, and in a second aspect, the replacement heart valve implant may further comprise a plurality of lashings securing the seal member to the tubular anchor member at some of the anchor member intersection points.

In addition or alternatively, and in a third aspect, the replacement heart valve implant may further comprise a plurality of stitches securing the plurality of valve leaflets to the seal member.

In addition or alternatively, and in a fourth aspect, the seal member includes a fabric strip fixedly attached to a polymeric seal element adjacent the inflow end of the tubular anchor member.

In addition or alternatively, and in a fifth aspect, the fabric strip is at least partially embedded in the polymeric seal element.

In addition or alternatively, and in a sixth aspect, the polymeric seal element is disposed radially outward of an outside surface of the tubular anchor member.

In addition or alternatively, and in a seventh aspect, a free end of the fabric strip folds back on itself adjacent the inflow end of the tubular anchor member to form a radially inner layer and a radially outer layer, the radially inner layer including the free end.

In addition or alternatively, and in an eighth aspect, a plurality of lashings secure the seal member to the tubular anchor member at some of the anchor member intersection points, each of the plurality of lashings including a securing element disposed between the radially inner layer and the radially outer layer.

In addition or alternatively, and in a ninth aspect, the securing element is a knot.

In addition or alternatively, and in a tenth aspect, the securing element is an adhesive.

In addition or alternatively, and in an eleventh aspect, the securing element is a portion of the lashing melted to itself to form a co-mingled bead of material.

In addition or alternatively, and in a twelfth aspect, the seal member extends longitudinally beyond the inflow end of the tubular anchor member.

In addition or alternatively, and in a thirteenth aspect, the end surface of each of the plurality of valve leaflets abuts the inner-facing surface of the seal member at a location longitudinally beyond the inflow end of the tubular anchor member.

In addition or alternatively, and in a fourteenth aspect, a replacement heart valve implant may comprise a tubular anchor member defining a longitudinal axis extending from an inflow end of the tubular anchor member to an outflow end of the tubular anchor member, a plurality of valve leaflets each defining a secured end and a free end opposite the secured end, wherein the free ends of the plurality of valve leaflets come together to define an outflow end of a valve, the plurality of valve leaflets being configured to shift between a deployed position wherein the outflow end of the valve is disposed within the tubular anchor member, and an everted position wherein the outflow end of the valve is disposed upstream of the tubular anchor member, and a seal member secured to the tubular anchor member at the inflow end of the tubular anchor member. The secured end of each of the plurality of valve leaflets is attached to the seal member adjacent the inflow end of the tubular anchor member. An end surface at the secured end of each of the plurality of valve leaflets faces toward the outflow end of the tubular anchor member when the plurality of valve leaflets is in the everted position.

In addition or alternatively, and in a fifteenth aspect, when the plurality of valve leaflets is in the everted position, the end surface at the secured end of each of the plurality of valve leaflets is disposed radially inward of the seal member.

In addition or alternatively, and in a sixteenth aspect, each of the plurality of valve leaflets is attached to the seal member at multiple locations along its secured end by one suture element.

In addition or alternatively, and in a seventeenth aspect, one suture element attaches all of the plurality of valve leaflets to the seal member at multiple locations along each one of the secured ends.

In addition or alternatively, and in an eighteenth aspect, a method of making a replacement heart valve implant may comprise attaching a plurality of valve leaflets, each valve leaflet having a free end and a secured end, to a seal member comprising a polymeric seal portion and a fabric strip fixedly attached to the polymeric seal portion, each valve leaflet being attached to the fabric strip by one suture element along the secured end to form a joint; folding a free end of the fabric strip back on itself to form an inner layer and an outer layer, wherein two sets of lashing holes disposed in the fabric strip on opposite sides of the joint align with each other and each valve leaflet adjoins the inner layer; positioning the inner layer against an outer surface of a tubular anchor member, the tubular anchor member including a plurality of anchor member intersection points distributed thereabout; and attaching the fabric strip at an inflow end of the tubular anchor member at some of the plurality of anchor member intersection points.

In addition or alternatively, and in a nineteenth aspect, attaching the fabric strip includes interweaving a lashing element through the two sets of aligned lashing holes and around one of the plurality of anchor member intersection points.

In addition or alternatively, and in a twentieth aspect, opposing ends of the lashing element are secured together to form a knot element, the knot element being disposed between the inner layer and the outer layer of the fabric strip.

The above summary of some embodiments, aspects, and/or examples is not intended to describe each disclosed embodiment or every implementation of the present disclosure. The Figures, and Detailed Description, which follow, more particularly exemplify these embodiments.

BRIEF DESCRIPTION OF THE DRAWINGS

The disclosure may be more completely understood in consideration of the following detailed description of various embodiments in connection with the accompanying drawings, in which.

Figure 1:
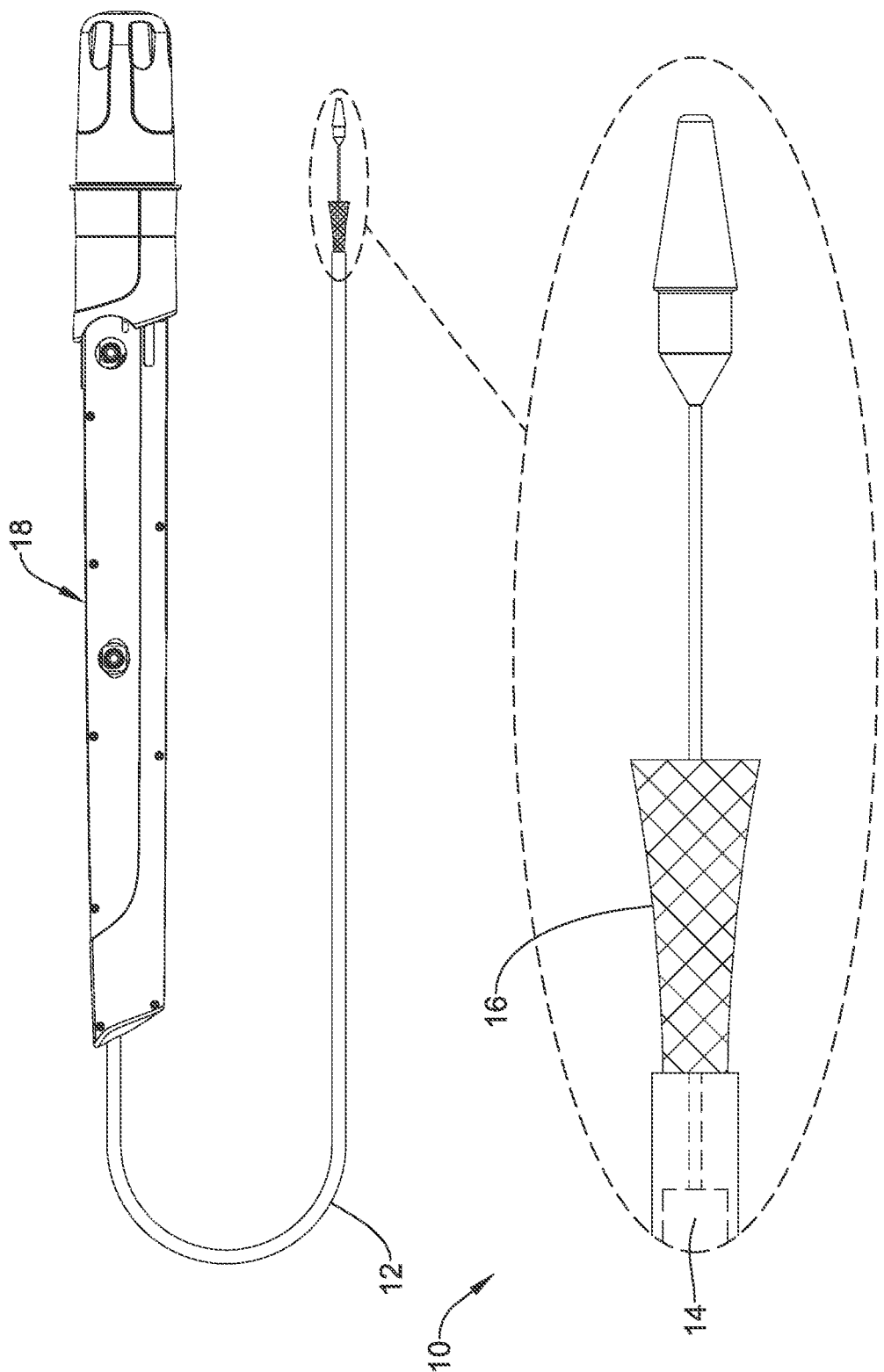
FIG. 1 schematically illustrates an example medical device system.

While aspects of the disclosure are amenable to various modifications and alternative forms, specifics thereof have been shown by way of example in the drawings and will be described in detail. It should be understood, however, that the intention is not to limit aspects of the disclosure to the particular embodiments described. On the contrary, the intention is to cover all modifications, equivalents, and alternatives falling within the spirit and scope of the disclosure.

DETAILED DESCRIPTION

The following description should be read with reference to the drawings, which are not necessarily to scale, wherein like reference numerals indicate like elements throughout the several views. The detailed description and drawings are intended to illustrate but not limit the claimed invention. Those skilled in the art will recognize that the various elements described and/or shown may be arranged in various combinations and configurations without departing from the scope of the disclosure. The detailed description and drawings illustrate example embodiments of the claimed invention.

For the following defined terms, these definitions shall be applied, unless a different definition is given in the claims or elsewhere in this specification.

All numeric values are herein assumed to be modified by the term "about," whether or not explicitly indicated. The term "about", in the context of numeric values, generally refers to a range of numbers that one of skill in the art would consider equivalent to the recited value (i.e., having the same function or result). In many instances, the term "about" may include numbers that are rounded to the nearest significant figure. Other uses of the term "about" (i.e., in a context other than numeric values) may be assumed to have their ordinary and customary definition(s), as understood from and consistent with the context of the specification, unless otherwise specified.

The recitation of numerical ranges by endpoints includes all numbers within that range, including the endpoints (e.g. 1 to 5 includes 1, 1.5, 2, 2.75, 3, 3.80, 4, and 5).

Although some suitable dimensions, ranges, and/or values pertaining to various components, features and/or specifications are disclosed, one of skill in the art, incited by the present disclosure, would understand desired dimensions, ranges, and/or values may deviate from those expressly disclosed.

As used in this specification and the appended claims, the singular forms "a", "an", and "the" include plural referents unless the content clearly dictates otherwise. As used in this specification and the appended claims, the term "or" is generally employed in its sense including "and/or" unless the content clearly dictates otherwise.

Relative terms such as "proximal", "distal", "advance", "retract", variants thereof, and the like, may be generally be considered with respect to the positioning, direction, and/or operation of various elements relative to a user/operator/manipulator of the device, wherein "proximal" and "retract" indicate or refer to closer to or toward the user and "distal" and "advance" indicate or refer to farther from or away from the user. Other relative terms, such as "upstream", "downstream", "inflow", and "outflow" refer to a direction of fluid flow within a lumen, such as a body lumen, a blood vessel, or within a device.

It is noted that references in the specification to "an embodiment", "some embodiments", "other embodiments", etc., indicate that the embodiment(s) described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it would be within the knowledge of one skilled in the art to effect such feature, structure, or characteristic in connection with other embodiments, whether or not explicitly described, unless clearly stated to the contrary. That is, the various individual elements described below, even if not explicitly shown in a particular combination, are nevertheless contemplated as being combinable or arrangable with each other to form other additional embodiments or to complement and/or enrich the described embodiment(s), as would be understood by one of ordinary skill in the art.

For the purpose of clarity, certain identifying numerical nomenclature (e.g., first, second, third, fourth, etc.) may be used throughout the description and/or claims to name and/or differentiate between various described and/or claimed features. It is to be understood that the numerical nomenclature is not intended to be limiting and is exemplary only. In some embodiments, alterations of and deviations from previously-used numerical nomenclature may be made in the interest of brevity and clarity. That is, a feature identified as a "first" element may later be referred to as a "second" element, a "third" element, etc. or may be omitted entirely, and/or a different feature may be referred to as the "first" element. The meaning and/or designation in each instance will be apparent to the skilled practitioner.

Diseases and/or medical conditions that impact the cardiovascular system are prevalent in the United States and throughout the world. Traditionally, treatment of the cardiovascular system was often conducted by directly accessing the impacted part of the system. For example, treatment of a blockage in one or more of the coronary arteries was traditionally treated using coronary artery bypass surgery. As can be readily appreciated, such therapies are rather invasive to the patient and require significant recovery times and/or treatments. More recently, less invasive therapies have been developed, for example, where a blocked coronary artery could be accessed and treated via a percutaneous catheter (e.g., angioplasty). Such therapies have gained wide acceptance among patients and clinicians.

Some relatively common medical conditions may include or be the result of inefficiency, ineffectiveness, or complete failure of one or more of the valves within the heart. For example, failure of the aortic valve or the mitral valve can have a serious effect on a human and could lead to serious health condition and/or death if not dealt with. Treatment of defective heart valves poses other challenges in that the treatment often requires the repair or outright replacement of the defective valve. Such therapies may be highly invasive to the patient. Disclosed herein are medical devices that may be used for delivering a medical device to a portion of the cardiovascular system in order to diagnose, treat, and/or repair the system. At least some of the medical devices disclosed herein may be used to deliver and implant a replacement heart valve (e.g., a replacement aortic valve, replacement mitral valve, etc.). In addition, the devices disclosed herein may deliver the replacement heart valve percutaneously and, thus, may be much less invasive to the patient. The devices disclosed herein may also provide a number of additional desirable features and benefits as described in more detail below.

The figures illustrate selected components and/or arrangements of a medical device system 10, shown schematically in FIG. 1 for example. It should be noted that in any given figure, some features of the medical device system 10 may not be shown, or may be shown schematically, for simplicity. Additional details regarding some of the components of the medical device system 10 may be illustrated in other figures in greater detail. A medical device system 10 may be used to deliver and/or deploy a variety of medical devices to a number of locations within the anatomy. In at least some embodiments, the medical device system 10 may include a replacement heart valve delivery system (e.g., a replacement aortic valve delivery system) that can be used for percutaneous delivery of medical implant 16, such as a replacement heart valve. This, however, is not intended to be limiting as the medical device system 10 may also be used for other interventions including valve repair, valvuloplasty, and the like, or other similar interventions.

The medical device system 10, as seen in FIG. 1 for example, may generally be described as a catheter system that includes a delivery system having an outer sheath 12 for a medical implant 16 (i.e., a replacement heart valve implant, for example, which term may be used interchangeably with the term "medical implant" herein) which may be coupled to the delivery system and disposed within a lumen of the outer sheath 12 during delivery of the medical implant 16. In some embodiments, the delivery system may include an inner catheter 14 extending at least partially through the outer sheath 12 (partially seen in phantom in FIG. 1). In some embodiments, the medical implant 16 may be coupled to the inner catheter 14 and disposed within the lumen of the outer sheath 12 during delivery of the medical implant 16. In some embodiments, a handle 18 may be disposed and/or attached at a proximal end of the delivery system, as seen in FIG. 1, and may include one or more actuation means associated therewith. In some embodiments, the handle 18 may be configured to manipulate the position of the outer sheath 12 relative to the inner catheter 14, and/or aid in the deployment of the medical implant 16. In some embodiments, the medical device system 10 may include a nose cone disposed at a distal end of a guidewire extension tube, wherein the guidewire extension tube may extend distally from the inner catheter 14. In at least some embodiments, the nose cone may be designed to have an atraumatic shape. In some embodiments, the nose cone may include a ridge or ledge that is configured to abut a distal tip of the outer sheath 12 during delivery of the medical implant 16.

Figure 2:
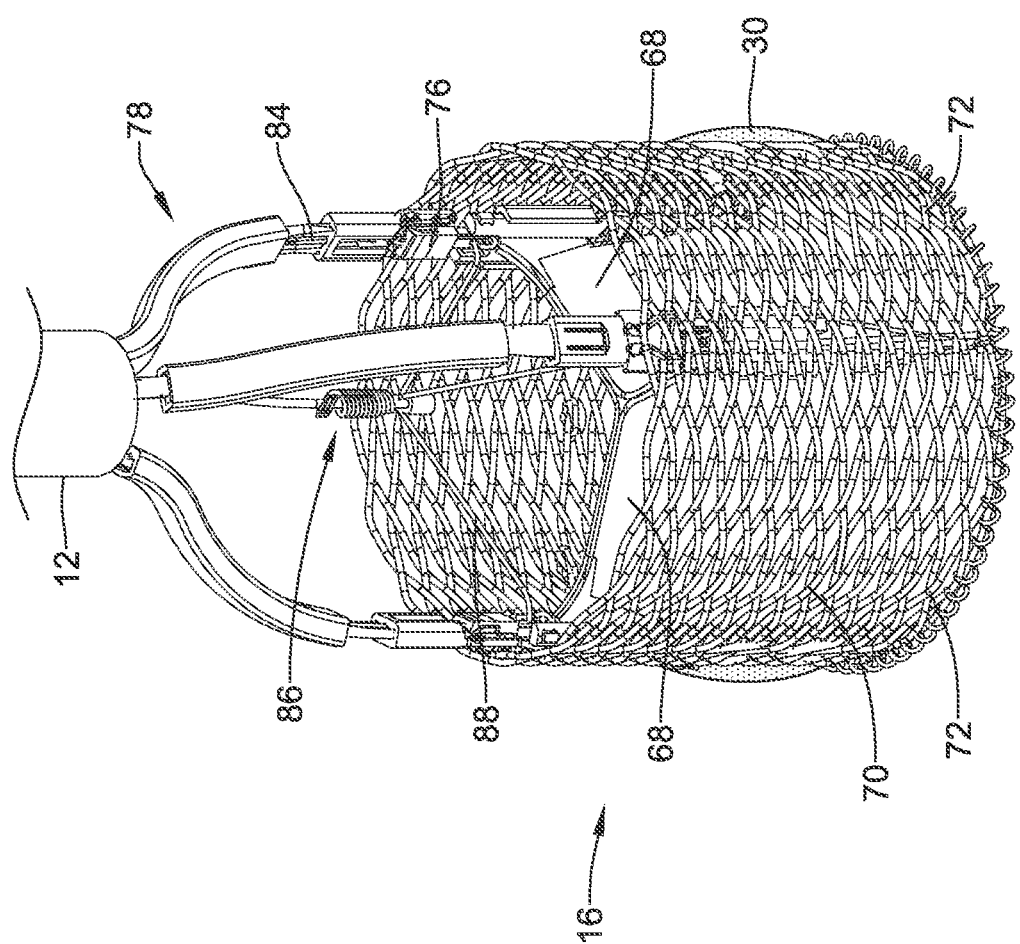
FIG. 2 is a perspective view of a portion of an example medical implant associated with the example medical device system.
Figure 3:
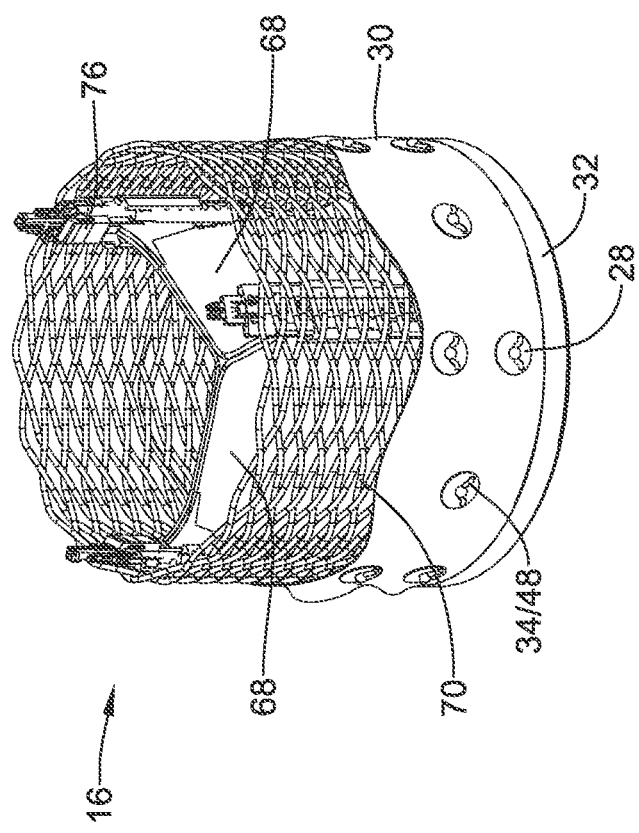
FIG. 3 is a perspective view of a portion of an example medical implant associated with the example medical device system.

In use, the medical device system 10 may be advanced percutaneously through the vasculature to a position adjacent to an area of interest and/or a treatment location. For example, in some embodiments, the medical device system 10 may be advanced through the vasculature to a position adjacent to a defective native valve (e.g., aortic valve, mitral valve, etc.). Alternative approaches to treat a defective aortic valve and/or other heart valve(s) are also contemplated with the medical device system 10. During delivery, the medical implant 16 may be generally disposed in an elongated and low profile "delivery" configuration within the delivery system and/or the outer sheath 12 coupled to and/or distal of the inner catheter 14. Once positioned, the outer sheath 12 may be retracted relative to the inner catheter 14, which may be held stationary by the handle 18, and/or the medical implant 16 to expose the medical implant 16. In some embodiments, the medical implant 16 may be disposed in an "everted" configuration or a partially-everted configuration while disposed within the lumen and/or the distal end of the outer sheath 12 and/or immediately upon exposure after retracting the outer sheath 12. In some embodiments, the "delivery" configuration and the "everted" configuration may be substantially similar and/or may be used interchangeably. The medical implant 16 may be actuated using the handle 18 in order to translate the medical implant 16 into a generally shortened and larger profile "deployed" configuration suitable for implantation within the anatomy, as seen in FIG. 2 for example. When the medical implant 16 is suitably deployed within the anatomy, the medical implant 16 may be released and/or detached from the medical device system 10 and the delivery system can be removed from the vasculature, thereby leaving the medical implant 16 in place in a "released" configuration, as seen in FIG. 3 for example, to function as, for example, a suitable replacement for the native valve. In at least some interventions, the medical implant 16 may be deployed within the native valve (e.g., the native valve is left in place and not excised). Alternatively, the native valve may be removed and the medical implant 16 may be deployed in its place as a replacement.

In some embodiments, the inner catheter 14 may include one or more lumens extending therethrough. For example, in some embodiments, the inner catheter 14 may include a first lumen, a second lumen, a third lumen, and a fourth lumen. Other configurations are also contemplated. In general, the one or more lumens extend along an entire length of the inner catheter 14. Other embodiments are contemplated, however, where one or more of the one or more lumens extend along only a portion of the length of the inner catheter 14. In some embodiments, a distal region of the inner catheter 14 may include a step in outer diameter that defines a decreased diameter section. In some embodiments, the decreased diameter section may define a region where other components of the medical device system 10 may be attached. For example, in some embodiments, a coupler assembly may be attached to the inner catheter 14 at the decreased diameter section and/or at a distal end of the inner catheter 14. In some embodiments, the coupler assembly may releasably couple the medical implant 16 to the inner catheter 14.

In some embodiments, disposed within one of the lumens of the inner catheter 14 may be at least one actuator member 84, which may be used to actuate (i.e., translate axially or longitudinally, and/or expand) the medical implant 16 between a delivery configuration and a deployed configuration. In some embodiments, the medical device system 10 may include at least one actuator member 84. In some embodiments, the at least one actuator member 84 may include a plurality of actuator members 84, two actuator members 84, three actuator members 84, four actuator members 84, or another suitable or desired number of actuator members 84. For the purpose of illustration only, the medical device system 10 and/or the medical implant 16 of FIG. 2 is configured to use three actuator members 84. In use, a proximal end of an actuator member 84 may be connected to the handle 18, and/or manipulated or otherwise actuated by a user using the handle 18, to shift the tubular anchor member 70 and/or the medical implant 16 from a "delivery" configuration to a "deployed" configuration, and later to a "released" configuration. During the release process for the medical implant 16, (e.g., as the medical implant 16 is actuated from the "delivery" configuration to the "deployed" configuration to the "released" configuration), the at least one actuator member 84 may be retracted, withdrawn, and/or translated proximally relative to the inner catheter 14, the medical implant 16, and/or the tubular anchor member 70.

In some embodiments, the actuator member 84 may be generally round, oblong, ovoid, rectangular, polygonal (i.e., two-sided, three-sided, four-sided, five-sided, six-sided, etc.) in shape. Other shapes, both regular and irregular, are also contemplated. In some embodiments, the actuator member 84 may be formed from a single piece of wire, round stock, or other suitable material, as discussed herein. In some embodiments, the actuator member 84 may be formed by further processing the single piece of wire, round stock, or other suitable material, such as by machining, stamping, laser cutting, etc. Some suitable but non-limiting materials for the actuator member 84, for example metallic materials or polymeric materials, may be described below.

It is to be noted that in order to facilitate understanding, certain features of the disclosure may be described in the singular, even though those features may be plural or recurring within the disclosed embodiment(s). Each instance of the features may include and/or be encompassed by the singular disclosure(s), unless expressly stated to the contrary. For example, a reference to "the actuator member", "the locking element", "the lumen", or other features may be equally referred to all instances and quantities beyond one of said feature. As such, it will be understood that the following discussion may apply equally to any and/or all of the components for which there are more than one within the medical implant 16 (i.e., the at least one actuator member, the plurality of locking elements, etc.) and/or the medical device system 10, unless explicitly stated to the contrary. Additionally, not all instances of some elements or features may be shown in each figure for clarity.

FIGS. 2-3 illustrate some selected components of the medical device system 10 and/or the medical implant 16 in the deployed (FIG. 2) and released (FIG. 3) configurations. For example, here it can be seen that the medical implant 16 includes a plurality of valve leaflets 68 (e.g., bovine pericardial, polymeric, etc.) which may be secured to a tubular anchor member 70 that is reversibly actuatable between an elongated "delivery" configuration, as in FIG. 1 for example, and an expanded "deployed" configuration. In some embodiments, the tubular anchor member 70 may include an inflow end and an outflow end. In some embodiments, the tubular anchor member 70 may form a tubular structure defining a central longitudinal axis extending from the inflow end of the tubular anchor member 70 to the outflow end of the tubular anchor member 70, and/or a lumen extending through the tubular anchor member 70 along, parallel to, coaxial with, and/or coincident with the central longitudinal axis. In some embodiments, the tubular anchor member 70 may be and/or include a braid formed from one or more filaments or wires (e.g., a single filament or wire, two filaments or wires, etc.). Other configurations are also contemplated. Some suitable but non-limiting materials for the tubular anchor member 70, for example metallic materials or polymeric materials, may be described below.

In some embodiments, the tubular anchor member 70 may include and/or form a plurality of anchor member intersection points 72 distributed around a circumference of the tubular anchor member 70. In some embodiments, the plurality of anchor member intersection points 72 may include two or more overlapping segments (e.g., a first segment, a second segment, a third segment, etc.) of the tubular anchor member 70 and/or the braid, filaments, wires, etc. thereof. In some embodiments, the two or more overlapping segments may be arranged in an alternating over-and-under pattern or arrangement. For example, at a first anchor member intersection point 72, a first segment may be disposed radially outward of a second segment. At an adjacent second anchor member intersection point 72 including the first segment, the first segment may be disposed radially inward of an overlapping segment (e.g., a third segment). If the first segment (or any single segment) is followed around the circumference of the tubular anchor member 70, the over-under-over pattern would continue alternating about the entire circumference of the tubular anchor member 70.

In some embodiments, the medical implant 16 may include a plurality of locking mechanisms 76 attached to the tubular anchor member 70, the plurality of locking mechanisms 76 being configured to secure the tubular anchor member 70 in the "deployed" and/or "released" configuration(s). In some embodiments, the at least one actuator member 84 may be configured to engage with the plurality of locking mechanisms 76 and actuate the tubular anchor member 70 and/or the medical implant 16 between the "delivery" configuration and the "deployed" configuration and/or the "released" configuration. In some embodiments, one actuator member 84 may correspond to, engage with, and/or actuate one locking mechanism 76. Other configurations are also contemplated. For example, in some embodiments, one actuator member 84 may correspond to, engage with, and/or actuate more than one locking mechanism 76.

In some embodiments, the plurality of locking mechanisms 76 may each comprise an axially movable post member, for example at the commissure portions of the valve leaflets 68 (the post member may sometimes be referred to as a "commissure post", which may serve to secure the plurality of valve leaflets 68, or the post member may be connected and/or attached to a commissure post), and a buckle member or other receiving element fixedly attached to the tubular anchor member 70 (e.g., along an interior surface of the tubular anchor member 70). In some embodiments, the buckle member or other receiving element may be configured to slidably receive the post member therein to engage with the buckle member and thereafter lock the tubular anchor member 70 and/or the medical implant 16 in the "deployed" and/or the "released" configuration(s). In some embodiments, each of the plurality of valve leaflets 68 may be secured to the tubular anchor member 70 at one post member. In some embodiments, each of the plurality of valve leaflets 68 may be secured to two adjacent post members at opposing sides of the valve leaflet 68. In at least some embodiments, a medical implant 16 may include a plurality of post members and a corresponding plurality of buckle members. Other configurations and correspondences are also contemplated. Some suitable but non-limiting materials for the buckle member and/or the post member, for example metallic materials or polymeric materials, may be described below.

In some embodiments, attachment between the medical implant 16 and the inner catheter 14 (and/or the outer sheath 12) may be effected through the use of a coupler assembly 78. The coupler assembly 78 may generally include a cylindrical base (not shown) that may be disposed about, attached to, and/or extending from a distal end of the inner catheter 14 (and/or the outer sheath 12). Projecting distally from the base is a plurality of fingers (e.g., two fingers, three fingers, four fingers, etc.) that are each configured to engage with the medical implant 16 at the buckle members (for example, at a proximal end of the buckle members), with the plurality of actuator members 84 extending therethrough and engaging the post members. A collar may be disposed about each of the fingers of the coupler assembly 78 to further assist in holding together the fingers and the buckle members. A guide may be disposed over each of the fingers proximal of the collar and may serve to keep the fingers of the coupler assembly 78 associated with the actuator members 84 extending adjacent to (and axially slidable relative to) the fingers of the coupler assembly 78. Finally, in some embodiments, a pin release assembly 86 may be a linking structure that keeps the post members, the buckle members, and the actuator members 84 associated with one another. The pin release assembly 86 may include a plurality of release pins 88 that may be joined together and held to a pin release mandrel. The pin release assembly 86 may not be present in all embodiments of the medical implant 16, and in at least some embodiments, the medical implant 16 may utilize one or more of various "pinless" release and/or locking mechanisms. Other suitable configurations are also contemplated. Some suitable but non-limiting materials for the coupler assembly 78, the fingers, the collars, the guides, and/or the pin release assembly 86, for example metallic materials or polymeric materials, may be described below.

During delivery, after the medical implant 16 is advanced within the anatomy to the desired location, the outer sheath 12 may be withdrawn (e.g., moved proximally relative to the inner catheter 14 and/or the medical implant 16) to expose the medical implant 16. Then, the actuator members 84 can be used to translate and "lock" the medical implant 16 in the "deployed" configuration by proximally retracting the actuator members 84 to pull the post members into engagement with the buckle members. Finally, in some embodiments, the plurality of release pins 88 can be removed, thereby decoupling the actuator members 84 from the post members, which allows the medical implant 16 to be released from the medical device system 10 and deployed in the anatomy in the "released" configuration. In some embodiments, the plurality of release pins 88 and/or the pin release assembly 86 may not be present, and other and/or alternative means of releasing the medical implant 16 may be utilized, such as a displacement-based or distance-based means of releasing the medical implant 16.

For simplicity and clarity purposes, not all elements of the disclosed invention are necessarily shown in each figure or discussed in detail below and/or the whole medical implant 16, the tubular anchor member 70, and/or other components may not be shown to facilitate understanding of certain elements. However, as discussed above, it will be understood that the following discussion may apply equally to any and/or all of the components for which there are more than one within the medical implant 16 (i.e., the plurality of actuator members 84, buckle members, post members, anchor element intersection points, etc.) and/or the medical device system 10.

In some embodiments, the plurality of valve leaflets 68 may be secured to the tubular anchor member 70 at, adjacent to, and/or using (at least in part) individual, corresponding post members. In some embodiments, the plurality of valve leaflets 68 may also be secured to the distal end of the tubular anchor member 70. In at least some embodiments, the distal end of the tubular anchor member 70 may be interchangeably described as the "inflow" end or the "upstream" end of the tubular anchor member 70 and/or the medical implant 16. In some embodiments, the plurality of valve leaflets 68 may be coupled and/or secured (i.e., to the post member, to the tubular anchor member 70, and/or back to themselves) using one or more sutures, threads, wires, filaments, or other suitable elements. In some embodiments, the plurality of valve leaflets 68 may be coupled and/or secured (i.e., to the post member, to the tubular anchor member 70, and/or back to themselves) using an adhesive, a bonding agent, or other suitable securing means. In some embodiments, the plurality of valve leaflets 68 may be coupled and/or secured (i.e., to the post member, to the tubular anchor member 70, and/or back to themselves) using a fabric strip, a textile, or other thin flexible material. In some embodiments, the plurality of valve leaflets 68 may not be directly attached to the tubular anchor member 70.

In some embodiments, the post members and/or the commissure posts may be secured and/or attached to the tubular anchor member 70 (e.g., along the interior of the tubular anchor member 70) with sutures, tethers, adhesives, or other suitable elements. In some embodiments, the commissure post and/or the post member may include one or more holes or other features provided to aid in securing and/or attaching the commissure post and/or the post member to the tubular anchor member 70. Positioned adjacent to (e.g., aligned with) the plurality of post members are a corresponding plurality of buckle members, which may be secured and/or fixedly attached to the tubular anchor member 70 (e.g., along the interior of the tubular anchor member 70) with sutures, adhesives, or other suitable mechanisms. In some embodiments, the post member may be axially translatable relative to the buckle member generally parallel to the central longitudinal axis of the tubular anchor member 70 when the post member is at least partially disposed within and/or engaged with the buckle member.

In some embodiments, one buckle member may be fixedly attached to the tubular anchor member 70 adjacent to each of the three post members and/or adjacent the proximal end of the tubular anchor member 70. Accordingly, in some embodiments, the tubular anchor member 70 may have a total of three buckle members and three post members attached thereto. Similarly, one actuator member 84 may be associated with each post member and buckle member, for a total of three actuator members 84 in the illustrated example(s). Other embodiments are contemplated where fewer or more buckle members, post members, and/or actuator members 84 may be utilized.

In some embodiments, a seal member 30 may be circumferentially disposed on and/or about a distal portion and/or an inflow portion of the tubular anchor member 70, as seen in FIGS. 2-3 for example, and as the term suggests, may help to seal an exterior of the medical implant 16 within and/or against a target site or area of interest upon deployment, thereby preventing leakage around the medical implant 16. In some embodiments, the seal member 30 may be disposed about and/or radially outward of an outside surface of the tubular anchor member 70. In some embodiments, the seal member 30 may be disposed around a perimeter and/or on or against an exterior surface of the tubular anchor member 70. In some embodiments, the seal member 30 may be coupled and/or secured at the distal end and/or the inflow end of the tubular anchor member 70.

In some embodiments, the seal member 30 may include a plurality of layers of polymeric material. Some suitable polymeric materials may include, but are not necessarily limited to, polycarbonate, polyurethane, polyamide, polyether block amide, polyethylene, polyethylene terephthalate, polypropylene, polyvinylchloride, polytetrafluoroethylene, polysulfone, and copolymers, blends, mixtures or combinations thereof. Other configurations and/or other suitable materials are also contemplated.

In some embodiments, the modulus of elasticity may vary and/or be different from layer to layer. In other embodiments, the elongation to break may vary and/or be different from layer to layer. In some embodiments, the seal member 30 may also include a reinforcement, a reinforcing layer, and/or one or more reinforcing members added to the polymeric material prior to curing. The reinforcement, the reinforcing layer, and/or the one or more reinforcing members may comprise a woven or nonwoven fabric and may be positioned within or between the various layers. In some embodiments, the reinforcement, the reinforcing layer, and/ or the one or more reinforcing members may be positioned on a radially innermost surface or radially outermost surface of the seal member 30. In some embodiments, the reinforcement, the reinforcing layer, and/or the one or more reinforcing members may be generally aligned. In some embodiments, the reinforcement, the reinforcing layer, and/or the one or more reinforcing members may be randomly oriented and/or disposed on the seal member 30.

Figure 4:
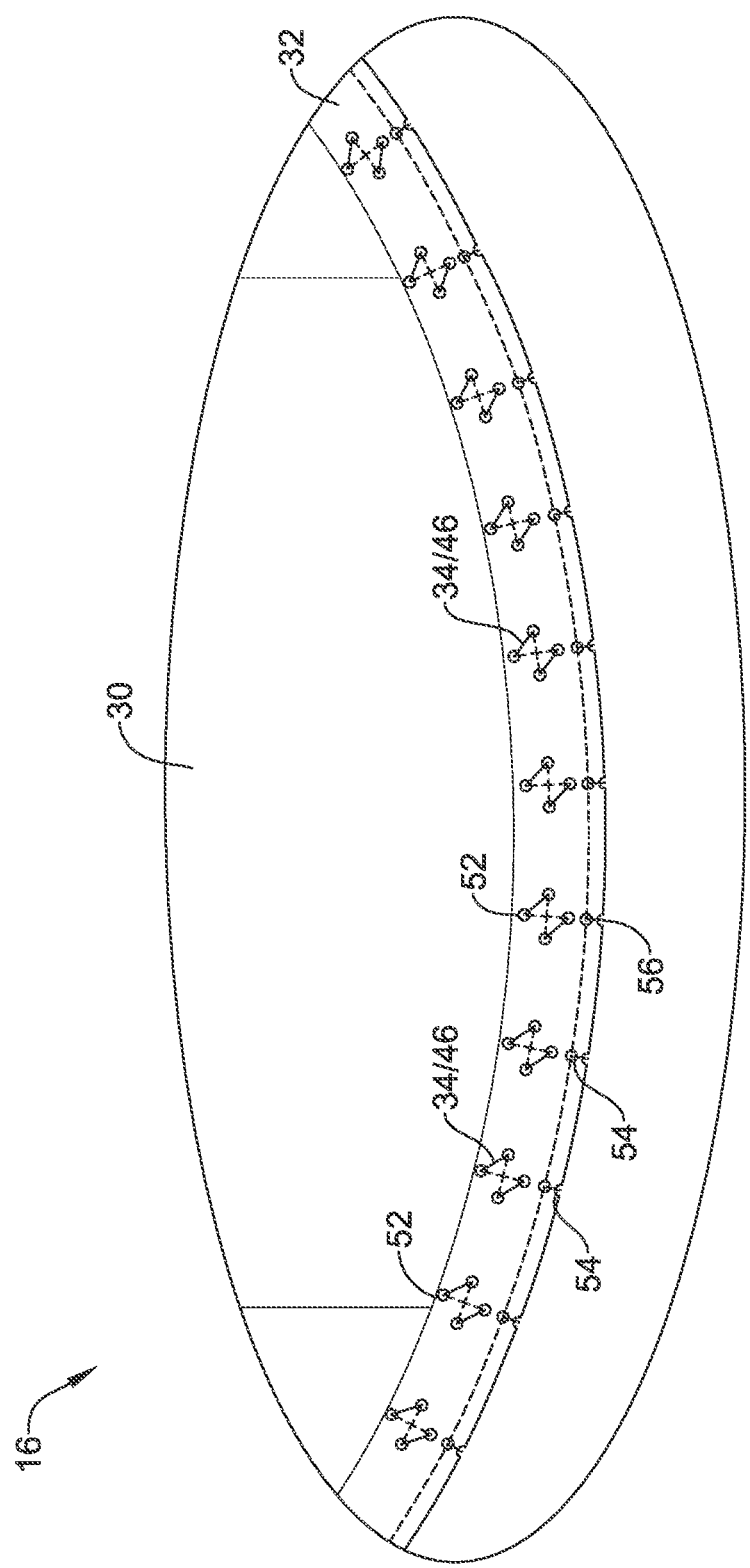
FIG. 4 illustrates selected portions of an example medical implant.
Figure 5:
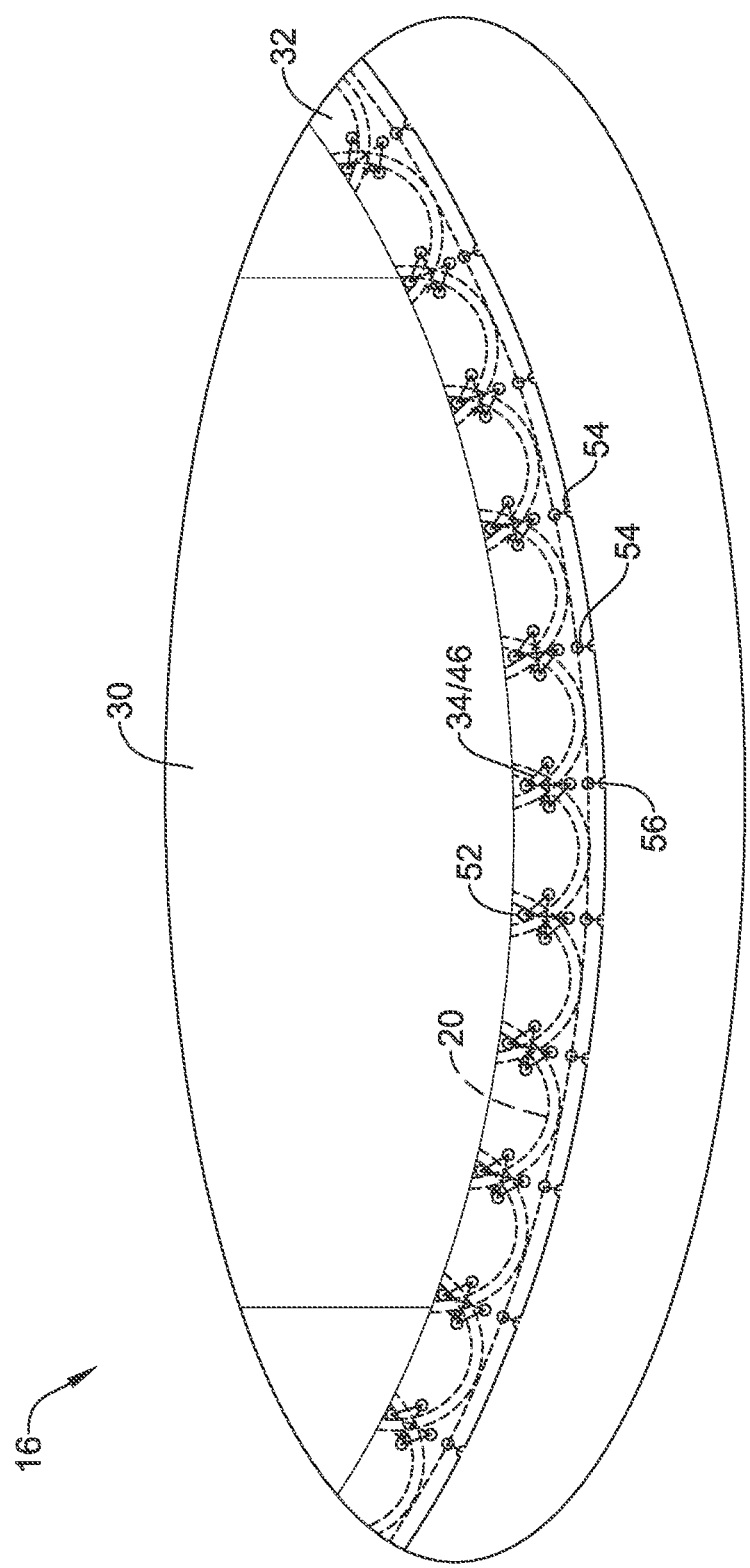
FIG. 5 illustrates selected portions of an example medical implant.

In some embodiments, a distal end of the seal member 30 may include a reinforcing band 32 fixedly attached to the seal member 30 at and/or adjacent the distal end and/or the inflow end of the tubular anchor member 70, as seen in FIGS. 4-5 for example. In some embodiments, the reinforcing band 32 may be integrally formed with, incorporated into, adhered to, and/or at least partially embedded within the seal member 30. In some embodiments, the reinforcing band 32 may be formed from a woven or nonwoven fabric strip, a textile, or other thin flexible material. The reinforcing band 32 may provide tear resistance in the vicinity of sutures, filaments, or other attachment elements associated with components or aspects of the medical implant 16. In some embodiments, the seal member 30 and/or the reinforcing band 32 may extend longitudinally beyond the distal end and/or the inflow end of the tubular anchor member 70.

In some embodiments, the medical implant 16 may include a plurality of lashings 34 securing the seal member 30 and/or the reinforcing band 32 to the tubular anchor member 70 at and/or adjacent the distal end and/or the inflow end of the tubular anchor member 70. In some embodiments, the plurality of lashings 34 may secure the reinforcing band 32 to the tubular anchor member 70 at some of the plurality of anchor member intersection points 72, as seen in FIG. 5 for example. In some embodiments, each of the plurality of lashings 34 may include a securing element 36. In some embodiments, the securing element 36 may be formed at least in part by connecting opposing ends of the lashing 34. In some embodiments, the securing element 36 may include a knot. In some embodiments, the securing element 36 may include an adhesive. In some embodiments, the securing element 36 may include a portion of the lashing 34 melted to itself to form a co-mingled bead of material.

Figure 6:
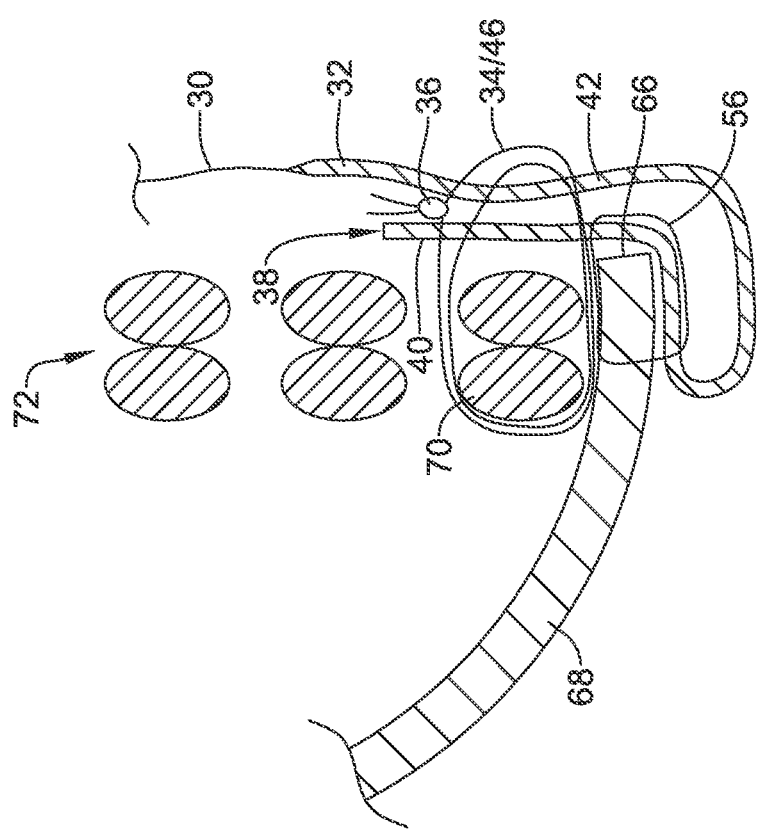
FIG. 6 is a partial section view of selected portions of an example medical implant.

In some embodiments, a free end 38 of the reinforcing band 32 may fold back on itself adjacent the distal end and/or the inflow end of the tubular anchor member 70 to form a radially inner layer 40 and a radially outer layer 42, as seen in FIG. 6 for example. In at least some embodiments, the radially inner layer 40 may include the free end 38. In at least some embodiments, the securing element 36 may be disposed radially between the radially inner layer 40 and the radially outer layer 42. In some embodiments, each of the plurality of valve leaflets 68 may include an end surface 66, wherein the end surface 66 of each of the plurality of valve leaflets 68 abuts an inner-facing surface of the seal member 30 and/or the reinforcing band 32. In some embodiments, the end surface 66 of each of the plurality of valve leaflets 68 abuts the inner-facing surface of the seal member 30 and/or the reinforcing band 32 at a location longitudinally beyond the distal end and/or the inflow end of the tubular anchor member 70.

In some embodiments, the plurality of valve leaflets 68 may each define a secured end and a free end opposite the secured end, wherein the free ends of the plurality of valve leaflets 68 come together to define an outflow end of a valve. In some embodiments, the secured end of each of the plurality of valve leaflets 68 may be directly attached to the seal member 30 and/or the reinforcing band 32 at and/or adjacent the distal end and/or the inflow end of the tubular anchor member 70. In some embodiments, the plurality of valve leaflets 68 may not be attached directly to the distal end and/or the inflow end of the tubular anchor member 70.

In some embodiments, the plurality of valve leaflets 68 may be configured to shift between a deployed position wherein the outflow end of the valve is disposed within the tubular anchor member 70, and an everted position wherein the outflow end of the valve is disposed outside of and/or upstream of the tubular anchor member 70. In at least some embodiments, the secured end includes the end surface 66.

Figure 7:
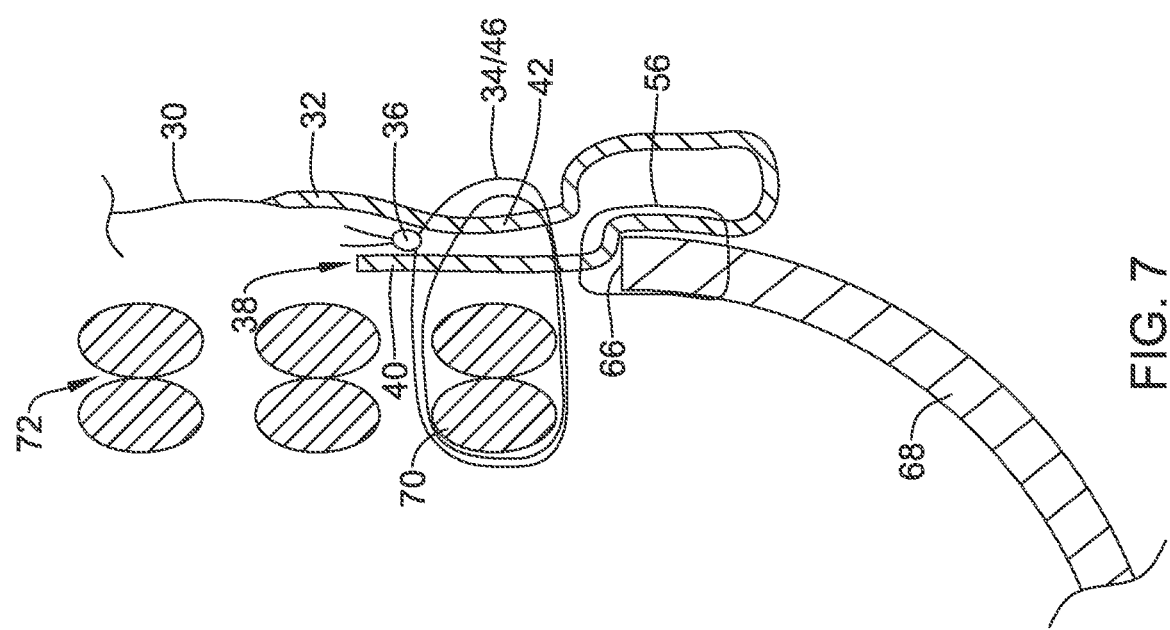
FIG. 7 is a partial section view of selected portions of an example medical implant.

In some embodiments, the end surface 66 at the secured end of each of the plurality of valve leaflets 68 faces toward the proximal end and/or the outflow end of the tubular anchor member 70 when the plurality of valve leaflets 68 is in the everted position, as seen in FIG. 7 for example. In some embodiments, when the plurality of valve leaflets 68 is in the everted position, the end surface 66 at the secured end of each of the plurality of valve leaflets 68 is disposed radially inward of the seal member 30, the reinforcing band 32, and/or the radially inner layer 40.

In some embodiments, each of the plurality of valve leaflets 68 is directly attached to the seal member 30, the reinforcing band 32, and/or the radially inner layer 40 at multiple locations along its secured end by one suture element 56 at a joint 44. In other words, in some embodiments, the medical implant 16 may have the same number of suture elements 56 as valve leaflets 68, wherein each suture element 56 extends between adjacent commissures and/or post members. In some embodiments, one suture element 56 directly attaches all of the plurality of valve leaflets 68 to the seal member 30, the reinforcing band 32, and/or the radially inner layer 40 at multiple locations along each one of the secured ends at a joint 44.

In some embodiments, each of the plurality of lashings 34 may be attached to and/or woven around two (or more) distinct overlapping segments of the tubular anchor member 70 at some of the plurality of anchor member intersection points 72, as seen in FIGS. 5-7 for example. In some embodiments, the two (or more) overlapping segments may be immediately adjacent each other where each of the plurality of lashings 34 is attached thereto, as seen in FIGS. 6-7 for example. In some embodiments, each of the plurality of lashings 34 may be directly attached to the two (or more) overlapping segments of the tubular anchor member 70. In some embodiments, at least a portion of the tubular anchor member 70 extends distally of the plurality of lashings 34. In some embodiments, at least a portion of the tubular anchor member 70 extends distally of all of the plurality of lashings 34. In some embodiments, at least a portion of each of the two (or more) overlapping segments extends distally of each of the plurality of lashings 34 attached thereto. In some embodiments, each of the plurality of lashings 34 includes a suture member. In some embodiments, each of the plurality of lashings 34 includes a lashing element and/or a securing element 36.

In some embodiments, the seal member 30 may include a plurality of perforations extending through the seal member 30 and/or the reinforcing band 32. In some embodiments, the plurality of perforations may include a first set of lashing holes 50, a second set of lashing holes 52, and/or a set of leaflet attachment holes 54. In some embodiments, the set of leaflet attachment holes 54 may be disposed along the radially inner layer 40 of the reinforcing band 32, and may be used to attach and/or to secure the plurality of valve leaflets 68 to the seal member 30 and/or the reinforcing band 32. In some embodiments, the set of leaflet attachment holes may be disposed between the first set of lashing holes 50 and the second set of lashing holes 52. In some embodiments, the second set of lashing holes 52 may mirror the first set of lashing holes 50 about the set of leaflet attachment holes 54. In some embodiments, the first set of lashing holes 50 may include two holes, three holes, four holes, five holes, six holes, or another suitable quantity of holes. In some embodiments, the second set of lashing holes 52 may include two holes, three holes, four holes, five holes, six holes, or another suitable quantity of holes. In an illustrated embodiment, the first set of lashing holes 50 may include four holes and the second set of lashing holes 52 may include four holes, but other configurations and/or arrangements are contemplated.

In some embodiments, the plurality of perforations may accommodate suture elements, lashing elements, filaments, etc. passing therethrough (e.g., through the reinforcing band 32 and/or the seal member 30) to secure elements or aspects of the medical implant 16, such as (but not limited to) the plurality of valve leaflets 68 and/or the tubular anchor member 70, for example. In some embodiments, the plurality of lashings 34 may extend through at least some of the plurality of perforations.

In some embodiments, one or more suture elements 56 may directly attach a distal end of the seal member 30 and/or the reinforcing band 32 to a distal end of the plurality of valve leaflets 68 at a joint 44 adjacent a distal end of the tubular anchor member 70, as seen in FIGS. 6-10 for example. In some embodiments, the one or more suture elements 56 may directly attach the reinforcing band 32 and/or a distal end of the reinforcing band 32 to the secured end of the plurality of valve leaflets 68 at a joint 44 adjacent the distal end and/or the inflow end of the tubular anchor member 70. In some embodiments, the set of leaflet attachment holes 54 may be disposed circumferentially along the joint 44. In some embodiments, the reinforcing band 32 (e.g., the fabric strip, etc.) may fold back on itself about and/or adjacent the joint 44 to form the radially inner layer 40 and the radially outer layer 42. In at least some embodiments, the joint 44 may be disposed distally of a distalmost end of the tubular anchor member 70. In some embodiments, the one or more suture elements 56 may include and/or form a plurality of square windings about the joint 44, as will be described herein. In some embodiments, the one or more suture elements 56 may be disposed distally of a distalmost filament, wire, anchor member intersection point 72, and/or element (e.g., crown) of the tubular anchor member 70.

In some embodiments, the plurality of lashings 34 may include a plurality of distal lashing sutures 46 and a plurality of proximal lashing sutures 48. In some embodiments, the plurality of distal lashing sutures 46 may directly attach a distal portion of the seal member 30 and/or the reinforcing band 32 (e.g., the fabric strip, etc.) to the tubular anchor member 70 at and/or adjacent the distal end and/or the inflow end of the tubular anchor member 70. In some embodiments, the plurality of distal lashing sutures 46 may attach the distal portion of the seal member 30 and/or the reinforcing band 32 (e.g., the fabric strip, etc.) at consecutive anchor member intersection points 72 at and/or adjacent the distal end and/or the inflow end of the tubular anchor member 70.

In some embodiments, the plurality of proximal lashing sutures 48 may attach a proximal portion of the seal member 30 to a distal portion of the tubular anchor member 70 proximal of the distal end and/or the inflow end of the tubular anchor member 70, as seen in FIG. 3 for example. In some embodiments, a grommet 28 may be disposed along an outer surface of the seal member 30 and/or at least partially embedded within the seal member 30 at each of the plurality of proximal lashing sutures 48 to aid in attaching the seal member 30 to the tubular anchor member 70. In some embodiments, the plurality of proximal lashing sutures 48 may extend through the grommet(s) 38. In some embodiments, the plurality of proximal lashing sutures 48 may attach the proximal portion of the seal member 30 to the distal portion of the tubular anchor member 70 at some of the anchor member intersection points 72. In some embodiments, the plurality of proximal lashing sutures 48 may attach the proximal portion of the seal member 30 to the tubular anchor member 70 at non-consecutive anchor member intersection points 72, as may be seen in FIG. 3 for example.

Figure 8:
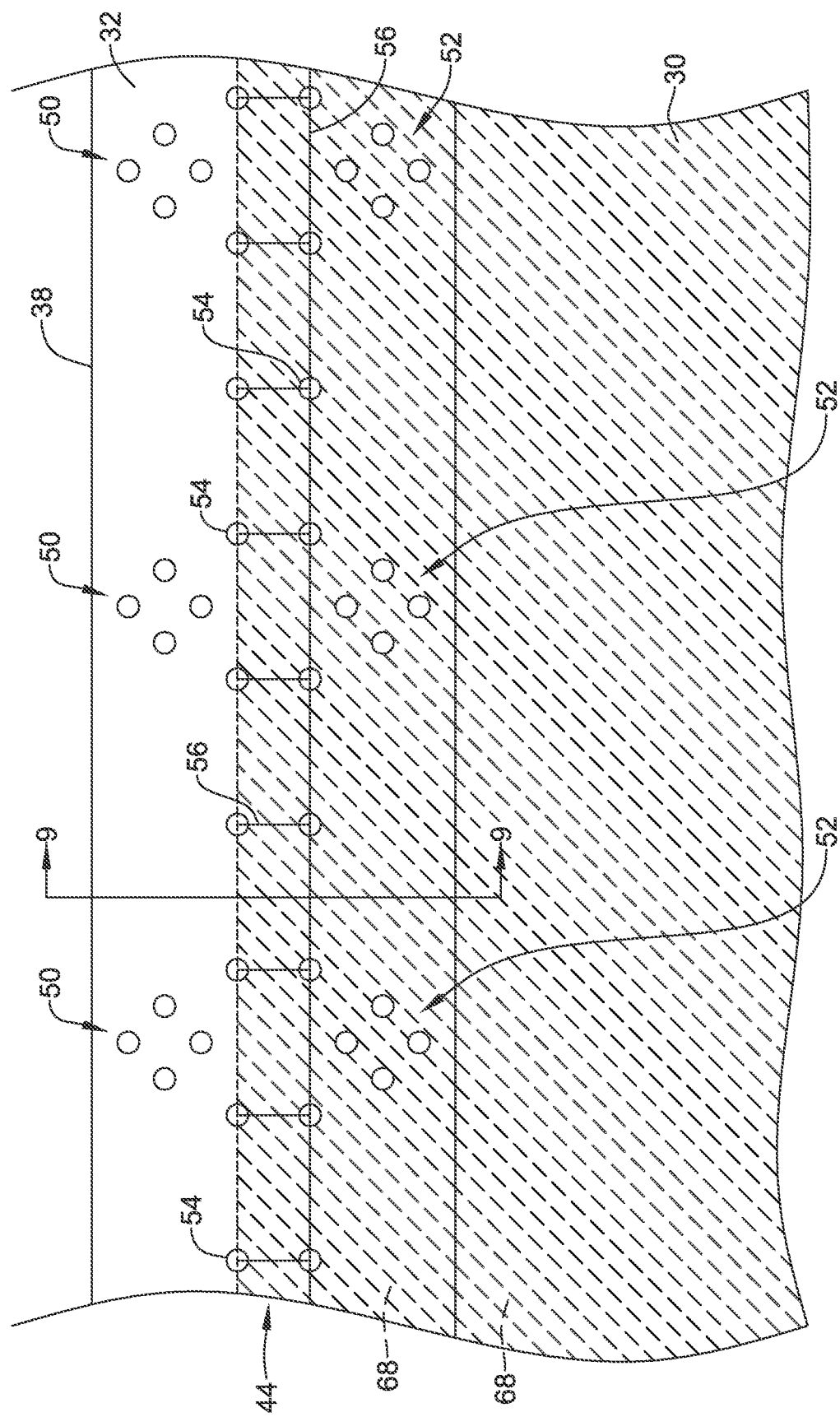
FIG. 8 is a flat pattern view of selected portions of an example medical implant.

In some embodiments, a method of making a medical implant 16 (e.g., a replacement heart valve implant, etc.) may include attaching a plurality of valve leaflets 68, each valve leaflet 68 having a free end and a secured end, to a seal member 30 comprising a polymeric seal portion and a reinforcing band 32 (e.g., a fabric strip, etc.) fixedly attached to the polymeric seal portion. In some embodiments, seal member 30 and/or the reinforcing band 32 (e.g., the fabric strip, etc.) may be laid out with the polymeric seal portion extending downward from the reinforcing band 32, such that all of the plurality of perforations are visible from the outside of the reinforcing band 32. In most embodiments, the seal member 30 and/or the reinforcing band 32 (e.g., the fabric strip, etc.) forms a generally tubular configuration. For simplicity of explanation, the method is described with respect to a portion of the seal member 30 and/or the reinforcing band 32 that is visible in a side view (e.g., a flat pattern view), as seen in FIG. 8 for example. The skilled artisan will understand that the seal member 30 and/or the reinforcing band 32 extends continuously in both side directions (e.g., circumferentially) until they meet to form the generally tubular configuration.

Figure 9:
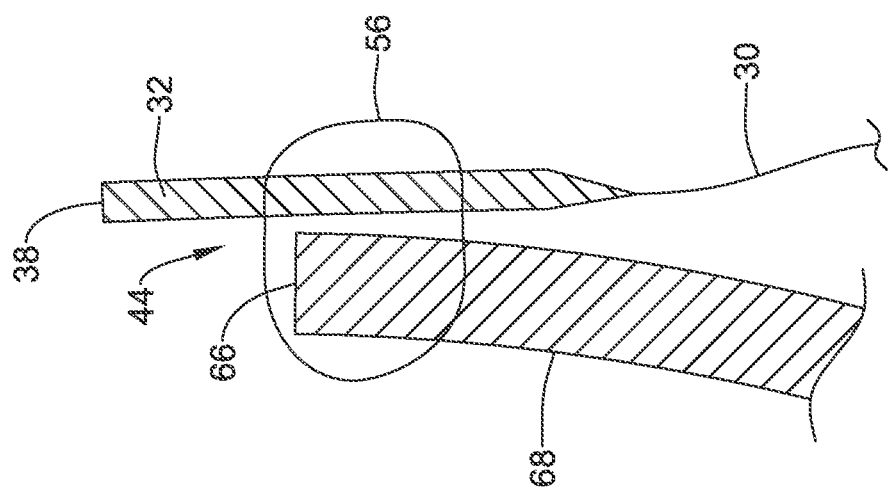
FIG. 9 is a partial section view of is a partial section view of selected portions of an example medical implant.

Each of the plurality of valve leaflets 68 may be positioned "behind" (e.g., radially inward from) the reinforcing band 32 (e.g., the fabric strip, etc.) and extending longitudinally downward from the seal member 30 and/or the reinforcing band 32 (e.g., the fabric strip, etc.), as seen from the outside (and as shown in FIGS. 8-9). The skilled artisan will recognize that the assembly process may be performed in an inverted orientation with the plurality of valve leaflets 68 extending upward and the relative orientations of elements as discussed herein reversed and/or shifted 180 degrees.

A suture element 56 of the one or more suture elements 56 may be inserted through (inserted radially inward through) a first hole of the set of leaflet attachment holes 54, for example at and/or adjacent a commissure and/or post member at a left end of one of the plurality of valve leaflets 68. The suture element 56 is passed through the seal member 30 and/or the reinforcing band 32 and the valve leaflet 68. In at least some embodiments, the set of leaflet attachment holes 54 may include a bottom row of holes that is substantially in line with one another along a circumference of the seal member 30 and/or the reinforcing band 32, and a top row of holes that is substantially in line with one another along a circumference of the seal member 30 and/or the reinforcing band 32. Next, the suture element 56 is passed to the right behind (radially inward of) the valve leaflet 68 to a second hole (e.g., the next hole in line) of the bottom row of holes in the set of leaflet attachment holes 54, where the suture element 56 is passed (radially outward) back through the valve leaflet 68 and the seal member 30 and/or the reinforcing band 32. Then the suture element 56 is passed upward to the top row of holes, which may be positioned longitudinally in line with the bottom row of holes and/or parallel to a central longitudinal axis of the seal member 30 and/or the reinforcing band 32, along an outer surface of the seal member 30 and/or the reinforcing band 32. The suture element 56 is inserted (radially inward) through one hole (for purposes of example, identified as a second hole corresponding to the second hole of the bottom row) of the top row of holes and passed through the seal member 30 and/or the reinforcing band 32 and the valve leaflet 68. The suture element 56 is passed downward behind (radially inward of) the valve leaflet 68 back to the second hole of the bottom row of holes. The suture element 56 is then passed back through (radially outward) the second hole of the bottom row of holes, thus forming a first square stitch of a plurality of square stitches along the joint 44. Each of the plurality of square stitches may be arranged generally within a plane along (e.g. coincident with and/or including) a radius extending outward from the central longitudinal axis of the seal member 30 and/or the reinforcing band 32.

Next, the suture element 56 is passed to the right in front of (radially outward of) the seal member 30 and/or the reinforcing band 32 to a third hole of the bottom row of holes. The suture element 56 is inserted (radially inward) through the third hole of the bottom row of holes and passed through the seal member 30 and/or the reinforcing band 32 and the valve leaflet 68. The suture element is passed upward behind (radially inward of) the valve leaflet 68 to the top row of holes. The suture element 56 is then passed back through (radially outward) the valve leaflet 68 and the seal member 30 and/or the reinforcing band 32 through a third hole of the top row of holes in the seal member 30 and/or the reinforcing band 32. The suture element 56 is passed downward along the outer surface (radially outward) of the valve leaflet 68 to the third hole of the bottom row of holes in the seal member 30 and/or the reinforcing band 32 and inserted back (radially inward) through the third hole of the bottom row of holes and through the seal member 30 and/or the reinforcing band 32 and the valve leaflet 68, thus forming a second square stitch of the plurality of square stitches along the joint 44.

Next, the suture element 56 is passed to the right behind (radially inward of) the valve leaflet to a fourth hole of the bottom row of holes, and the above discussed pattern (first square stitch, second square stitch) is repeated until an adjacent commissure or post member is reached at a right end of the valve leaflet 68. Upon reaching the adjacent commissure or post member at the right end of the valve leaflet 68, the suture element 56 is alternatingly passed back through the bottom row of holes in the seal member 30 and/or the reinforcing band 32 (e.g., the fabric strip, etc.) and the valve leaflet 68 (in, out, in, out, etc.) until the first hole is again reached, at which location the suture element 56 is secured to itself with a knot, adhesive, etc. The above discussed process may be repeated for each valve leaflet 68.

In some embodiments, each valve leaflet 68 may be attached to the reinforcing band 32 (e.g., the fabric strip, etc.) by one suture element 56 along the secured end to form the joint 44. In other words, a medical implant 16 have three valve leaflets 68 may also include three suture elements 56. In some embodiments, all of the plurality of valve leaflets 68 may be attached to the seal member 30 and/or the reinforcing band 32 (e.g., the fabric strip, etc.) with one suture element 56.

Figure 10:
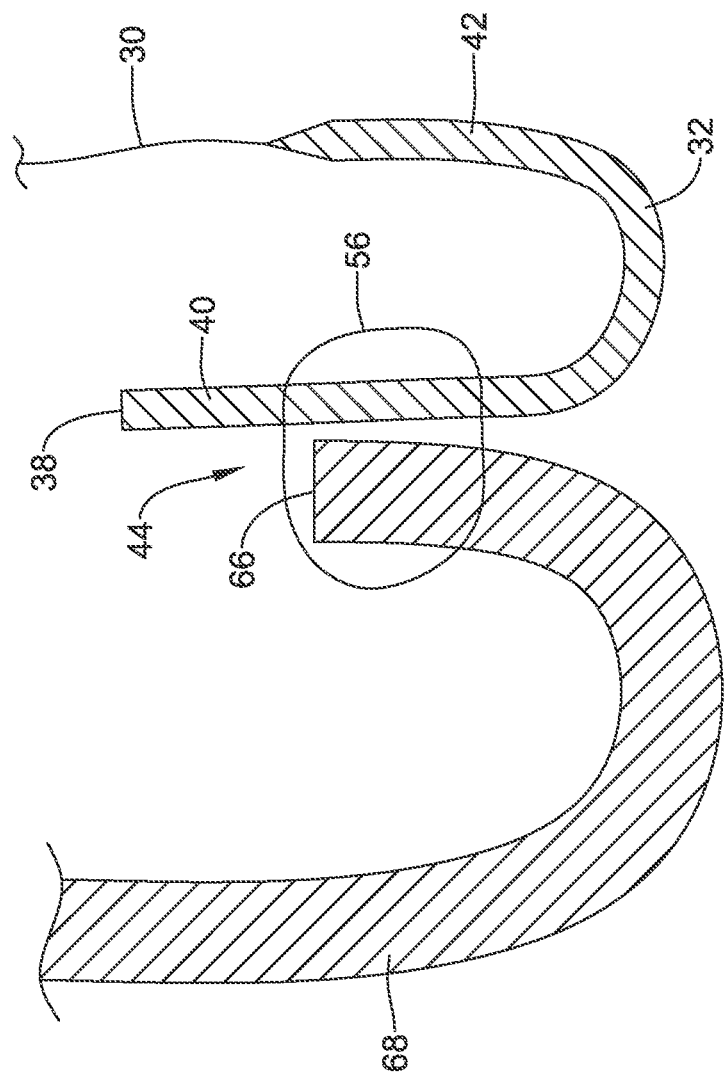
FIG. 10 is a partial section view of selected portions of an example medical implant.

In some embodiments, after attaching the plurality of valve leaflets 68 to the seal member 30 and/or the reinforcing band 32 (e.g., the fabric strip, etc.), a method of making a medical implant 16 (e.g., a replacement heart valve implant, etc.) may include folding a free end 38 of the reinforcing band 32 (e.g., the fabric strip, etc.) back on itself to form a radially inner layer 40 and a radially outer layer 42, as seen in FIG. 10 for example, wherein two sets of lashing holes (e.g., the first set of lashing holes 50 and the second set of lashing holes 52) disposed in the reinforcing band 32 (e.g., the fabric strip, etc.) on opposite sides of the joint 44 align with each other and each valve leaflet 68 adjoins the radially inner layer 40.

In some embodiments, a method of making a medical implant 16 (e.g., a replacement heart valve implant, etc.) may also include positioning the radially inner layer 40 against an outer surface of a tubular anchor member 70, the tubular anchor member 70 including a plurality of anchor member intersection points 72 distributed thereabout.

In some embodiments, a method of making a medical implant 16 (e.g., a replacement heart valve implant, etc.) may also include attaching the reinforcing band 32 (e.g., the fabric strip, etc.) at an inflow end of the tubular anchor member 70 at some of the plurality of anchor member intersection points 72 using a plurality of lashings 34 and/or a plurality of lashing elements. In some embodiments, attaching the reinforcing band 32 (e.g., the fabric strip, etc.) may include interweaving a distal lashing suture 46 (e.g., a lashing element) through the two sets of aligned lashing holes and around one of the plurality of anchor member intersection points 72.

In some embodiments, the distal lashing suture(s) 46, as seen from the outside of the medical implant 16 and/or the seal member 30 and/or the reinforcing band 32 (e.g., the fabric strip, etc.), may form and/or be arranged with two parallel segments visible against an outer surface of the seal member 30 and/or the reinforcing band 32 (e.g., the fabric strip, etc.). When interweaving the distal lashing suture(s) 46, the distal lashing suture(s) 46 may cross behind the anchor member intersection point 72 between opposing lashing holes, which may be arranged in a diamond or square-shaped pattern, for example. In some embodiments, opposing ends of the distal lashing suture 46 (e.g., the lashing element, etc.) may be secured together to form a securing element 36 (e.g., a knot element, etc.). In some embodiments, the securing element 36 (e.g., the knot element, etc.) may be disposed between the radially inner layer 40 and the radially outer layer 42 of the reinforcing band 32 (e.g., the fabric strip, etc.).

The materials that can be used for the various components of the medical device system 10 (and/or other systems disclosed herein) and the various elements thereof disclosed herein may include those commonly associated with medical devices. For simplicity purposes, the following discussion makes reference to the delivery system and/or the medical implant 16. However, this is not intended to limit the devices and methods described herein, as the discussion may be applied to other elements, members, components, or devices disclosed herein, such as, but not limited to, the tubular anchor member 70, the actuator member 84, the locking mechanism 76, the post member, the buckle member, and/or elements or components thereof.

In some embodiments, the delivery system and/or the medical implant 16, and/or components thereof (such as, but not limited to, the tubular anchor member 70, the locking mechanisms 76, the actuator members 84, etc.), may be made from a metal, metal alloy, polymer (some examples of which are disclosed below), a metal-polymer composite, ceramics, combinations thereof, and the like, or other suitable material. Some examples of suitable metals and metal alloys include stainless steel, such as 304V, 304L, and 316LV stainless steel; mild steel; nickel-titanium alloy such as linear-elastic and/or super-elastic nitinol; other nickel alloys such as nickel-chromium-molybdenum alloys (e.g., UNS: N06625 such as INCONEL® 625, UNS: N06022 such as HASTELLOY® C-22®, UNS: N10276 such as HASTELLOY® C276®, other HASTELLOY® alloys, and the like), nickel-copper alloys (e.g., UNS: N04400 such as MONEL® 400, NICKELVAC® 400, NICORROS® 400, and the like), nickel-cobalt-chromium-molybdenum alloys (e.g., UNS: R30035 such as MP35-N® and the like), nickel-molybdenum alloys (e.g., UNS: N10665 such as HASTELLOY® ALLOY B2®), other nickel-chromium alloys, other nickel-molybdenum alloys, other nickel-cobalt alloys, other nickel-iron alloys, other nickel-copper alloys, other nickel-tungsten or tungsten alloys, and the like; cobalt-chromium alloys; cobalt-chromium-molybdenum alloys (e.g., UNS: R30003 such as ELGILOY®, PHYNOX®, and the like); platinum enriched stainless steel; titanium; combinations thereof; and the like; or any other suitable material.

As alluded to herein, within the family of commercially available nickel-titanium or nitinol alloys, is a category designated "linear elastic" or "non-super-elastic" which, although may be similar in chemistry to conventional shape memory and super elastic varieties, may exhibit distinct and useful mechanical properties. Linear elastic and/or non-super-elastic nitinol may be distinguished from super elastic nitinol in that the linear elastic and/or non-super-elastic nitinol does not display a substantial "superelastic plateau" or "flag region" in its stress/strain curve like super elastic nitinol does. Instead, in the linear elastic and/or non-super-elastic nitinol, as recoverable strain increases, the stress continues to increase in a substantially linear, or a somewhat, but not necessarily entirely linear relationship until plastic deformation begins or at least in a relationship that is more linear than the super elastic plateau and/or flag region that may be seen with super elastic nitinol. Thus, for the purposes of this disclosure linear elastic and/or non-super-elastic nitinol may also be termed "substantially" linear elastic and/or non-super-elastic nitinol.

In some cases, linear elastic and/or non-super-elastic nitinol may also be distinguishable from super elastic nitinol in that linear elastic and/or non-super-elastic nitinol may accept up to about 2-5% strain while remaining substantially elastic (e.g., before plastically deforming) whereas super elastic nitinol may accept up to about 8% strain before plastically deforming. Both of these materials can be distinguished from other linear elastic materials such as stainless steel (that can also be distinguished based on its composition), which may accept only about 0.2 to 0.44 percent strain before plastically deforming.

In some embodiments, the linear elastic and/or non-super-elastic nickel-titanium alloy is an alloy that does not show any martensite/austenite phase changes that are detectable by differential scanning calorimetry (DSC) and dynamic metal thermal analysis (DMTA) analysis over a large temperature range. For example, in some embodiments, there may be no martensite/austenite phase changes detectable by DSC and DMTA analysis in the range of about −60 degrees Celsius (° C.) to about 120° C. in the linear elastic and/or non-super-elastic nickel-titanium alloy. The mechanical bending properties of such material may therefore be generally inert to the effect of temperature over this very broad range of temperature. In some embodiments, the mechanical bending properties of the linear elastic and/or non-super-elastic nickel-titanium alloy at ambient or room temperature are substantially the same as the mechanical properties at body temperature, for example, in that they do not display a super-elastic plateau and/or flag region. In other words, across a broad temperature range, the linear elastic and/or non-super-elastic nickel-titanium alloy maintains its linear elastic and/or non-super-elastic characteristics and/or properties.

In some embodiments, the linear elastic and/or non-super-elastic nickel-titanium alloy may be in the range of about 50 to about 60 weight percent nickel, with the remainder being essentially titanium. In some embodiments, the composition is in the range of about 54 to about 57 weight percent nickel. One example of a suitable nickel-titanium alloy is FHP-NT alloy commercially available from Furukawa Techno Material Co. of Kanagawa, Japan. Other suitable materials may include ULTANIUM™ (available from Neo-Metrics) and GUM METAL™ (available from Toyota). In some other embodiments, a superelastic alloy, for example a superelastic nitinol can be used to achieve desired properties.

In at least some embodiments, portions or all of the delivery system and/or the medical implant 16, and/or components thereof, may also be doped with, made of, or otherwise include a radiopaque material. Radiopaque materials are understood to be materials capable of producing a relatively bright image on a fluoroscopy screen or another imaging technique during a medical procedure. This relatively bright image aids a user in determining the location of the delivery system and/or the medical implant 16. Some examples of radiopaque materials can include, but are not limited to, gold, platinum, palladium, tantalum, tungsten alloy, polymer material loaded with a radiopaque filler, and the like. Additionally, other radiopaque marker bands and/or coils may also be incorporated into the design of the delivery system and/or the medical implant 16 to achieve the same result.

In some embodiments, a degree of Magnetic Resonance Imaging (MRI) compatibility is imparted into the medical implant 16. For example, the delivery system and/or the medical implant 16, and/or components or portions thereof, may be made of a material that does not substantially distort the image and create substantial artifacts (i.e., gaps in the image). Certain ferromagnetic materials, for example, may not be suitable because they may create artifacts in an MRI image. The delivery system and/or the medical implant 16, or portions thereof, may also be made from a material that the MM machine can image. Some materials that exhibit these characteristics include, for example, tungsten, cobalt-chromium-molybdenum alloys (e.g., UNS: R30003 such as ELGILOY®, PHYNOX®, and the like), nickel-cobalt-chromium-molybdenum alloys (e.g., UNS: R30035 such as MP35-N® and the like), nitinol, and the like, and others.

In some embodiments, a sheath or covering (not shown) may be disposed over portions or all of the delivery system and/or the medical implant 16. The sheath may be made from a polymer or other suitable material. Some examples of suitable polymers may include polytetrafluoroethylene (PTFE), ethylene tetrafluoroethylene (ETFE), fluorinated ethylene propylene (FEP), polyoxymethylene (POM, for example, DELRIN® available from DuPont), polyether block ester, polyurethane (for example, Polyurethane 85A), polypropylene (PP), polyvinylchloride (PVC), polyetherester (for example, ARNITEL® available from DSM Engineering Plastics), ether or ester based copolymers (for example, butylene/poly(alkylene ether) phthalate and/or other polyester elastomers such as HYTREL® available from DuPont), polyamide (for example, DURETHAN® available from Bayer or CRISTAMID® available from Elf Atochem), elastomeric polyamides, block polyamide/ethers, polyether block amide (PEBA, for example available under the trade name PEBAX®), ethylene vinyl acetate copolymers (EVA), silicones, polyethylene (PE), Marlex high-density polyethylene, Marlex low-density polyethylene, linear low density polyethylene (for example REXELL®), polyester, polybutylene terephthalate (PBT), polyethylene terephthalate (PET), polytrimethylene terephthalate, polyethylene naphthalate (PEN), polyetheretherketone (PEEK), polyimide (PI), polyetherimide (PEI), polyphenylene sulfide (PPS), polyphenylene oxide (PPO), poly paraphenylene terephthalamide (for example, KEVLAR®), polysulfone, nylon, nylon-12 (such as GRILAMID® available from EMS American Grilon), perfluoro(propyl vinyl ether) (PFA), ethylene vinyl alcohol, polyolefin, polystyrene, epoxy, polyvinylidene chloride (PVdC), poly(styrene-b-isobutylene-b-styrene) (for example, SIBS and/or SIBS 50A), polycarbonates, ionomers, biocompatible polymers, other suitable materials, or mixtures, combinations, copolymers thereof, polymer/metal composites, and the like. In some embodiments the sheath can be blended with a liquid crystal polymer (LCP). For example, the mixture can contain up to about 6 percent LCP.

It should be understood that this disclosure is, in many respects, only illustrative. Changes may be made in details, particularly in matters of shape, size, and arrangement of steps without exceeding the scope of the invention. This may include, to the extent that it is appropriate, the use of any of the features of one example embodiment being used in other embodiments. The invention's scope is, of course, defined in the language in which the appended claims are expressed.

What is claimed is:

1. A replacement heart valve implant, comprising:
   a tubular anchor member defining a longitudinal axis extending from an inflow end of the tubular anchor member to an outflow end of the tubular anchor member;
   a plurality of valve leaflets each defining a secured end and a free end opposite the secured end, wherein the free ends of the plurality of valve leaflets come together to define an outflow end of a valve, the plurality of valve leaflets being configured to shift between a deployed position wherein the outflow end of the valve is disposed within the tubular anchor member, and an everted position wherein the outflow end of the valve is disposed upstream of the tubular anchor member; and
   a seal member secured to the tubular anchor member at the inflow end of the tubular anchor member;
   wherein the secured end of each of the plurality of valve leaflets is attached to the seal member adjacent the inflow end of the tubular anchor member;
   wherein an end surface at the secured end of each of the plurality of valve leaflets faces toward the outflow end of the tubular anchor member when the plurality of valve leaflets is in the everted position.

2. The replacement heart valve implant of claim 1, wherein when the plurality of valve leaflets is in the everted position, the end surface at the secured end of each of the plurality of valve leaflets is disposed radially inward of the seal member.

3. The replacement heart valve implant of claim 1, wherein each of the plurality of valve leaflets is attached to the seal member at multiple locations along its secured end by one suture element.

4. The replacement heart valve implant of claim 1, wherein one suture element attaches all of the plurality of valve leaflets to the seal member at multiple locations along each one of the secured ends.

5. A replacement heart valve implant, comprising:
   a tubular anchor member actuatable between a delivery configuration and a deployed configuration, the tubular anchor member including an inflow end, an outflow end, and a plurality of anchor member intersection points, and defining a longitudinal axis extending from the inflow end of the tubular anchor member to the outflow end of the tubular anchor member;
   a plurality of valve leaflets; and a seal member secured to the tubular anchor member at the inflow end of the tubular anchor member and extending beyond the inflow end,
wherein the seal member includes a fabric strip fixedly attached to a polymeric seal element adjacent the inflow end of the tubular anchor member,
wherein the fabric strip is at least partially embedded in the polymeric seal element,
wherein a plurality of lashings secures the seal member to the tubular anchor member at some of the anchor member intersection points, each of the plurality of lashings have at least one securing element disposed between a radially inner layer and a radially outer layer,
wherein the at least one securing element is selected from the group consisting of a knot, an adhesive, and a portion of the lashing melted to itself to form a co-mingled bead of material,
wherein a plurality of stitches secures the plurality of valve leaflets to the seal member,
wherein an end surface of each of the plurality of valve leaflets abuts an inner-facing surface of the seal member.

\* \* \* \* \*